United States Patent [19]

Weder et al.

[11] Patent Number: 4,731,210

[45] Date of Patent: Mar. 15, 1988

[54] PROCESS FOR THE PREPARATION OF LIPOSOMAL MEDICAMENTS

[75] Inventors: Hans G. Weder, Langnau; Otmar N. Zumbühl, Wolfenschiessen; Reto A. Schwendener, Arosa; Maximilian Asanger, Zurich, all of Switzerland

[73] Assignee: Hans Georg Weder, Zurich, Switzerland

[21] Appl. No.: 337,806

[22] Filed: Jan. 7, 1982

[30] Foreign Application Priority Data

Jan. 7, 1981 [CH] Switzerland ............................. 53/81

[51] Int. Cl.$^4$ ........................... A61K 9/52; B01J 13/02
[52] U.S. Cl. ...................................... 264/4.3; 264/4.1; 264/4.6; 424/450; 428/402.2; 436/829
[58] Field of Search ................. 252/316; 424/38, 450; 436/829; 264/4.1, 4.6, 4.3; 428/402.2

[56] References Cited

U.S. PATENT DOCUMENTS

| | | | |
|---|---|---|---|
| 3,932,657 | 1/1976 | Rahman | 424/319 |
| 3,957,971 | 5/1976 | Oleniacz | 424/70 |
| 3,993,754 | 11/1976 | Rahman et al. | 424/177 |
| 4,310,506 | 1/1982 | Baldeschwieler et al. | 424/1 |

OTHER PUBLICATIONS

Rhoden et al.: "Formation of Unilamellar Lipid Vesicles . . . ", Biochemistry, vol. 18, No. 19, 1979, pp. 4173-4176.

Primary Examiner—Richard D. Lovering
Attorney, Agent, or Firm—Millen & White

[57] ABSTRACT

Associates of at least one amphiphilic bilayer-forming substance and a solubilizing agent are formed in an aqueous phase. The bilayer-forming substance itself can be a pharmaceutical substance, or pharmaceutical substances and/or pharmaceutical auxiliaries may be added. The equilibrium conditions for the molar ratio of bilayer-forming substance to solubilizing agent in the associates are then changed in the aqueous phase containing the associates, in order to remove solubilizing agent from the associates, so that the associates combine to form liposomes. In particular, the solubilizing agent concentration in the aqueous phase is reduced, for example by dilution with additional aqueous phase. The change is effected at a rate which is sufficiently high for formation of liposomes having a predefined number of double layers. Furthermore, the rate of change in the aqueous phase is kept virtually constant with respect to location and time. The liposomes thereby achieve a predefined, virtually homogeneous size.

4 Claims, No Drawings

PROCESS FOR THE PREPARATION OF LIPOSOMAL MEDICAMENTS

BACKGROUND OF THE INVENTION

The present invention relates to a process for the preparation of liposomal medicaments which are associates of at least one amphiphilic bilayer-forming substance and a solubilizing agent. These are formed in an aqueous phase optionally with the addition of pharmaceutical substances and/or of pharmaceutical auxiliaries.

Amphiphilic bilayer-forming substances are substances which have both polar (hydrophilic) and nonpolar (lipophilic) properties and which form bilayers (double layers) in an aqueous phase.

Liposomes are spherical structures with a diameter of from 20 nm to a few μm. They consist of at least one double layer and enclose a certain, aqueous volume. Depending on the number of double layers enclosing the aqueous inner volume, unilamellar (one double layer), oligolamellar (a few double layers) and multilamellar (many double layers) liposomes are defined.

In contrast to unilamellar liposomes, in which an aqueous inner volume corresponding to their size is enclosed, oligolamellar and multilamellar liposomes enclose several separate aqueous inner volumes according to the number of double layers.

On the basis of their physico-chemical properties and their structure, liposomes can be used as carriers for pharmaceutical substances. These substances are incorporated in or bonded to either the aqueous inner volume or the lipophilic double layers as a result of their hydrophilic and/or lipophilic properties.

When pharmacodynamically and/or biologically active bilayer-forming agents are used, the liposome itself is the medicament. The liposomal medicaments can be converted into appropriate galenical forms of administration, depending on the mode of administration.

For controlled medication, liposomal medicaments can be used for therapeutic and/or diagnostic purposes and as depot medicament forms. Furthermore, conversion of a pharmaceutical substance into a liposomal medicament can produce an improvement in the stability of the pharmaceutical substance and in the resulting galenical form of administration.

Known processes for the preparation of liposomes and liposomal medicaments include:

1. Shaking and/or acoustic irradiation of amphiphilic bilayer-forming substances, optionally with the addition of pharmaceutical substances and/or pharmaceutical auxiliaries, in an aqueous phase.
2. Injection of amphiphilic bilayer-forming substances, dissolved in organic solvents, such as ethanol or ether, into an aqueous medium, pharmaceutical substances and/or pharmaceutical auxiliaries optionally being present.
3. Acoustic irradiation of a system consisting of an aqueous phase and an organic phase, which contains amphiphilic, bilayer-forming substances, and removal of the organic solvent by evaporation, optionally in the presence of pharmaceutical substances and/or pharmaceutical auxiliaries.
4. Dissolution of amphiphilic, bilayer-forming substances in an aqueous medium using solubilizing agents, mixed micelles or associates being formed, and subsequent removal of the solubilizing agent from the aqueous medium by means of gel chromatography or equilibrium dialysis.

However, all of these preparation processes have at least one in most cases several of the following disadvantages. Thus, each severe preparation process, such as, for example, ultrasonic irradiation, inevitably leads to partial degradation of the amphiphilic, bilayer-forming substances and of the pharmaceutical substances, such as, for example, proteins and peptides, to be enclosed in the liposome. If organic solvents are used, removal of these from the liposomal medicament formed is only incomplete. Likewise, it is not possible using these processes to prepare liposomal medicaments which are homogeneous with respect to the degree of dispersion in particle size of the liposomes contained therein—vesicle sizes of 20 nm to several thousand nm thereby occur—and/or with respect to the number of double layers enclosing the inner, aqueous phase of the liposomes. Exact metering of the pharmaceutical substances present in the liposomal medicament is thus scarcely possible.

It is frequently only possible to use very dilute dispersions, so that, if the liposomal medicament formed is to be present in a concentration required for medication, it becomes necessary subsequently to concentrate the medicament by means of expensive processes, usually ultrafiltration.

The known processes are also unsuitable for the preparation of liposomal medicaments on production scales. Further separation processes, such as ultracentrifugation and/or fractional filtration, must in most cases subsequently also be carried out to achieve the indispensable increase in homogeneity, whether with respect to the degree of dispersion or to the number of double layers enclosing the aqueous phase of a liposome.

The in vivo properties of liposomal medicaments are decisively influenced by the degree of dispersion of the liposomes contained therein and by the number of double layers which enclose the inner aqueous phase of the liposomes. Thus, high blood level values are achieved over a relatively long period with homogeneous, unilamellar liposomes having a diameter corresponding to the maximum pore size in the sinusoidal capillary area (about 100 nm). In contrast, the blood level values of smaller or larger unilamellar liposomes decrease significantly, and, in particular, the liver level values correspondingly increase. There is also the possibility of controlling the distribution of homogeneous unilamellar liposomes in certain organs, such as the spleen, kidney or lung, via their size. The in vivo properties of polydisperse unilamellar liposomal medicaments cannot be characterized, so that controlled medication is not possible. The in vivo properties of multilamellar, in most cases extremely polydisperse liposomes is characterized in that the liposomes become concentrated, above all, in the liver, spleen and lung, which means that extremely low blood levels result.

SUMMARY OF THE INVENTION

It is, accordingly, an object of this invention to provide a process which largely avoids the mentioned degradation of the amphiphilic bilayer-forming substances and of the pharmaceutical substances, and which enables preparation, as rapidly as possible and if desired continuously, of liposomal medicaments which are free from toxic solvents and have an extremely high homogeneity (e.g., variances of ±4%) with respect to size distribution and a defined number of double layers; and in an amount necessary for medication and with a required content of pharmaceutical substance.

Upon further study of the specification and appended claims, further objects and advantages of this invention will become apparent to those skilled in the art.

These objects have been achieved by this invention by providing such a process wherein in the aqueous phase containing the associates, the equilibrium conditions for the molar ratio of the bilayer-forming substance and the solubilizing agent in the associates, is changed, in the sense of an increase in this ratio, at a rate which is high enough for the associates to combine to form liposomes having a defined number of double layers, and which is virtually constant, so that the liposomes formed have a defined, virtually homogeneous size.

DETAILED DESCRIPTION

The present invention is based on the discovery that associates from which the solubilizing agent is removed combine to form liposomes, the size of which depends on the rate at which the solubilizing agent is withdrawn or, more fundamentally, on the rate at which the equilibrium conditions are changed to effect an increase in the molar ratio of bilayer-forming substance to solubilizing agent in the associates. Experiments, which will be described below, have shown that unilamellar liposomes with a minimum size for a given system can be obtained if the equilibrium conditions are changed virtually instantaneously, for example by sudden dilution of the aqueous phase (in which case the concentration of solubilizing agent in the aqueous phase is suddenly reduced). If the equilibrium conditions are changed more slowly, larger liposomes are obtained, the size of which is then virtually constant if the equilibrium conditions are changed at a rate which remains virtually constant (e.g., meaning ±2%, throughout this text) with respect to time and location (i.e., at all the associates in the aqueous phase). If the change in equilibrium conditions is effected at a constant rate which is just lower than a first upper threshold rate at which unilamellar liposomes of maximum size are formed, and which can be determined empirically by routine preliminary experiments, liposomes with a defined plurality of double layers are formed, the size distribution still being homogeneous. By "defined" is meant that the number of double layers in essentially all liposomes will be the same and this number will be predeterminable, in view of routine preliminary experiments, by adjustment in rate of change of equilibrium conditions. However, this rate should not fall below a second, lower threshold rate of change of equilibrium conditions, which likewise can easily be determined by routine preliminary experiments in each individual case, since liposomes which no longer have a defined number of double layers and have a heterogeneous size distribution are formed below this second threshold rate.

Thus, for any given system (specific bilayer-forming substance(s); specific solubilizing agent(s); specific additive(s); specific amounts of these; etc.), the specific rates of equilibrium change necessary to achieve any given combination of liposome size, homogeneity and number of double layers are determined routinely by preliminary experiments. The same is true for the minimum rate necessary to achieve desired properties.

The same is also true for details of any of methods A-D described below, e.g., with respect to conditions and compositions of solutions or other components which are combined in order to achieve intended effects, e.g., addition of two associate solutions to achieve equilibrium conditions which result in liposomes of sizes and compositions of a predetermined nature. The same holds for the constancy of the rate of change of the equilibrium conditions. The stringency of this requirement is determinable by similar routine preliminary experiments in which constancy of rate is varied. Results of such parametric preliminary experiments are detailed below.

Some of the various possible embodiments of the invention are illustrated below.

Preferably, to prepare associates, amphiphilic, bilayer-forming substances can first be converted into a solid state having as large as possible a surface and, optionally with the addition of pharmaceutical substances and/or pharmaceutical auxiliaries. This conversion can be achieved in a known manner by dissolving such substances, in organic solvents or mixtures thereof, and then evaporating off the solvents, so that, for example, an appropriately thin film of the solid substance mixture is formed on the glass wall of a round-bottomed flask, or then removing the solvents by lyophilization (freeze-drying).

The solubilizing agents necessary for formation of the associates in aqueous solution can be either added directly to the organic phase or dissolved in the aqueous phase which subsequently will be added to the highly disperse solid substance mixture. If necessary, both the organic solvent mixture and the aqueous phase can contain the solubilizing agents. An aqueous phase of defined ionic strength (preferably of about 0 to about 0.3) and defined pH value (preferably of about 1 to about 10) is then added in an amount which is preferably just sufficient for the associates formed therein to be kept in solution. Suitably, the pH value is maintained by addition of a buffer mixture. The concentration of this buffer is not critical, amounts effective to maintain the pH value sufficing. The selected ionic strength can be kept by addition of the necessary amount of neutral salts such as sodium chloride. Pharmaceutical substances and/or pharmaceutical auxiliaries which are readily soluble in water can also be contained directly in the aqueous phase to be added.

The associate solution can contain about 1 to 150, preferably 10 to 100 mg/ml of bilayer-forming substance and about 1 to 200, preferably 5 to 100 mg/ml of solubilizing agent. The molar ratio of bilayer-forming substance to solubilizing agent is suitably about 0.1 to 2.

In the aqueous phase containing the associates, the equilibrium conditions for the molar ratio of bilayer-forming substance to solubilizing agent in the associates must now be changed, i.e., an increase in this ratio must be effected. For this purpose, it is possible, for example, A. to reduce the total concentration of solubilizing agent in the aqueous phase by dilution of the aqueous phase, or B. to remove the solubilizing agent from the associate by chemical and/or physico-chemical reactions of the solubilizing agent in the aqueous phase, or C. to reduce the total concentration of solubilizing agent by countercurrent dialysis of the aqueous phase, or D. to increase the total concentration of bilayer-forming substance in the aqueous phase by adding bilayer-forming substance.

The term "total concentration of the solubilizing agent" in this context means the total content, based on the aqueous phase, of solubilizing agents in the aqueous phase and in the associates.

To prepare liposomal medicaments by means of dilution (A), the aqueous phase containing the associates can be diluted with an additional amount of aqueous phase in a manner such that the concentration of the solubilizing agent is reduced to preferably less than 25% of the starting concentration (the starting concentration preferably being not higher or not substantially higher (e.g., by up to 10%) than that required to solubilize the total amount of bilayer-forming agent). Solubilizing agent is thereby removed from the associates, which causes restructuring of the bilayer-forming substances to form double layers, by which means liposomes or liposomal medicaments are formed. Preferably, the aqueous phase to be added likewise consists of buffer solution with added salts such as sodium chloride. Generally, the pH value of the aqueous phase is between about 1 and about 10, preferably between 5 and 8; its ionic strength is between 0 and about 0.3.

Preferably, the added aqueous phase has the same constitution as that of the aqueous phase which contains the associates except for the content of solubilizer component in the latter.

If a sufficient quantity of the solubilizing agents is present in or added to the highly disperse solid substance mixture described above, and if formation of the associates is instantaneous when the aqueous phase is added, formation of the liposomes or of the liposomal medicaments can be achieved immediately by simply adding a sufficient amount, preferably about 2 to 25 parts by volume, of aqueous phase to one part by volume of the highly disperse substance mixture. A subsequent concentration step can be necessary.

The size of the liposomes contained in the liposomal medicament can be controlled, for example, by choosing the absolute concentration of amphiphilic bilayer-forming substances, and/or by varying the molar ratio between the bilayer-forming substance and the solubilizing agent, and/or by choosing the solubilizing agent or agents or the mixing ratios thereof. Corresponding results are summarized in the table in Example 1.

Furthermore, the size of the liposomes depends on the time of the dilution process, i.e., on the rate of dilution; suitably, the total time to final dilution is on the order of about 10 msec. (practically immeasurably short) to about 3 hours.

In the preparation of liposomal medicaments, the temperature should preferably be chosen such that the associates form as rapidly as possible in the aqueous phase, and that their stability until the subsequent dilution step is ensured. The dilution is advantageously carried out at a temperature about 5° to 25° C. above the corresponding transition temperatures of the amphiphilic bilayer-forming substances. The transition temperature of a bilayer-forming substance is the temperature of the crystal/liquid crystal phase transition of the double layers formed in the aqueous phase. Generally, the working temperature is about 0° to about 100° C., preferably 10° to 70° C. These considerations of temperature apply to all mole ratio changing methods of this invention.

Preparation of liposomal medicaments by chemical and/or physico-chemical inactivation (B) of the solubilizing agent in the aqueous phase containing the associates can be effected as follows, for example:

a. A sudden change in temperature (jump in temperature) in the aqueous phase, whereupon the solubility of the solubilizing agents is greatly reduced and/or the interaction forces between the solubilizing agent and the bilayer-forming substances are influenced, and solubilizing agent is thus removed from the associates. Generally, the jump in temperature includes a change from a temperature which is about 5° to 25° C. above the transition temperature, to a temperature which is as low as possible below this transition temperature, particularly from temperatures of about 30° to 100° C. to temperatures of about 0° to 20° C.

b. Addition of suitable adsorbents, such as activated carbon, silica gels, finely dispersed silicic acid, which come into contact with the aqueous phase. The solubilizing agents present in the aqueous phase and in the associates can thereby be removed.

c. Sudden change in pH value (jump in pH) of the aqueous phase, whereupon the solubilizing agents are removed from the aqueous phase, for example by precipitation. This can be achieved by addition of acid (e.g. hydrochloric acid), base (e.g. sodium hydroxide solution) or acidic or basic ion exchangers. The individual conditions depend largely on the $pK_a$ value of the solubilizing agent.

d. Addition of a further substance to the aqueous phase which leads to complexing and/or precipitation of the solubilizing agents contained therein. This can be effected, for example, by precipitating cationic or anionic solubilizing agents by means of structurally suitable anionic or cationic substances (a quaternary ammonium salt precipitates virtually all anionic solubilizing agents).

Preparation of liposomal medicaments by countercurrent dialysis (C) requires a semipermeable membrane which as completely as possible retains the amphiphilic bilayer-forming substances in the aqueous phase to be dialysed, but has a high permeability to the solubilizing agents. Furthermore, the semipermeable membrane should be such that it retains the desired amount of pharmaceutical substances and/or pharmaceutical auxiliaries contained in the aqueous phase to be dialysed. These semipermeable membranes are preferably membranes of cellulose, hydrated cellulose, regenerated cellulose (e.g. cellophane) or cellulose derivatives, such as acetyl cellulose, the thickness of which is within the $\mu m$ range and which have a molecular exclusion limit within the molecular weight range of from 1,000 to 10,000. Furthermore, membranes of polyamides (nylon), polyenes, such as polyethylene or polypropylene, polyesters, polyvinyl chloride, polytetrafluoroethylene and polycarbonate are suitable.

The preferred membrane thickness is about 5 to about 20 $\mu m$.

When the aqueous phase to be dialysed and the dialysing liquid, separated from one another by the membrane described above, flow countercurrently along a forced route in as low as possible a layer thickness, (preferably 0.1 to 1 mm) the solubilizing agent is removed very rapidly, and if desired also completely (<1% of the starting concentration) from the aqueous phase to be dialysed, whereupon the liposomal medicament is formed.

The flow of the dialysing liquid is preferably controlled such that the concentrations of the substances to be dialysed increase continuously in the direction of flow of the dialysing liquid. The flow rate of the dialysing liquid can advantageously be chosen such that the concentration gradient, formed via the semipermeable membrane, of the substances to be dialysed is as large as possible.

This countercurrent dialysis method fulfills the prerequisite of maintaining contact between the aqueous phase to be dialysed and the dialysing liquid via the semipermeable membrane until formation of the liposomal medicaments has ended and the solubilizing agents contained therein have been reduced to the desired concentration. Generally, this is achieved after about 1 to 120 minutes.

Compared with the process known hitherto, this flow process has the distinct advantage that liposomes or liposomal medicaments which are extremely homogeneous in respect of size distribution and of the number of double layers enclosing the inner aqueous phase can be prepared extremely rapidly and continuously by reducing the concentration of solubilizing agent in the aqueous phase at a high rate which is virtually constant (with respect to location and time), it being possible to avoid any dilution of the resulting medicament, and for the preparation process to be continuously monitored. The rate of dialysis of the solubilizing agents and thus the size of the liposomes formed can be controlled by suitably choosing the ratio of flow rates of the aqueous phase to be dialysed and of the dialysing liquid (preferably about 1:6 to 1:10), in that the size of the liposomes formed decreases as the flow rate in the dialysing liquid increases in comparison with the flow rate of the aqueous phase to be dialysed. Furthermore, the size of liposomes, as already described, can be controlled by choosing the concentrations, the molar ratios and the nature of the solubilizing agent in a manner similar to that described above with respect to the dilution method.

In U.S. patent application Ser. No. 224,993, filed on Jan. 14, 1981, now U.S. Pat. No. 4,438,052, whose disclosure is incorporated by reference herein, there is described a process for producing bilayer vesicles by means of flow-through dialyses. This process differs from the present counter-current dialysis process since it includes a stationary phase whereas in the present process both phases are flowing. The older process thus cannot be operated continuously, in contrast to the present process.

Preparation of liposomal medicaments by increasing the bilayer-forming agent concentration (D) in the aqueous phase which contains the associates and optionally pharmaceutical substances and/or pharmaceutical auxiliaries can be carried out as follows: a film or a lyophilisate of bilayer-forming substances can be prepared as described above, optionally with the additives mentioned. An aqueous phase which already contains associates of bilayer-forming substance and solubilizing agent as well as solubilizing agents which are not bonded in associates and pharmaceutical substances and optionally pharmaceutical auxiliaries can then be added. By subsequent careful shaking, the bilayer-forming substances of the lipid film or of the lyophilisate can then be converted into associates by means of the solubilizing agent still free in the aqueous phase, whereupon a new molar ratio of bilayer-forming substances to solubilizing agents is established in favor of the bilayer-forming agents, in comparison with the aqueous phase originally added, and liposomal medicaments are thus spontaneously formed.

A further possibility consists in first converting amphiphilic bilayer-forming substances into associates as described, in two separate vessels, and establishing a new equilibrium between the bilayer-forming substances and the solubilizing agents in favor of the bilayer-forming substances by mixing the two associate solutions. If the same solubilizing agents are used for preparing the two associate solutions, but in different concentrations, a new ratio of bilayer-forming agent to solubilizing agent is automatically established after the two associate solutions are mixed, which in turn, with suitable choice of solubilizing agents, leads to the formation of liposomal medicaments. If different, structurally suited solubilizing agents are used for the preparation of the two associate solutions, it is possible completely or partially to inactivate the solubilizing agents by chemical and/or physico-chemical reactions between the two when the two solutions are mixed, which leads spontaneously to formation of liposomal medicaments. If solubilizing agents with different solubilizing properties are added to the amphiphilic bilayer-forming substances for the preparation of the two associate solutions, so that the solubilizing agents employed are capable of solubilizing only the bilayer-forming agent of the original associate solutions when the two associate solutions are mixed, a new molar ratio between the bilayer-forming substances and the solubilizing agents in favor of the bilayer-forming substances is established in the two associates as a result of transfer of the bilayer-forming substances between the two associates, which leads to formation of liposomal medicaments.

In all of the methods A–D, routine preliminary experiments can be used to determine details, of all steps, which will be effective for the specific purpose involved.

Suitable bilayer-forming substances include, particularly, phospholipids, for instance phosphoglycerides (diesters, monoesters, diethers, monoethers wherein the ester and ether groups preferably are of 8 to 24 carbon atoms each) such as lecithins (phosphatidylcholines), kephalins (phosphatidyl-ethanolamines, phosphatidylserines), inositolphosphatides, phosphatidylic acids, phosphatidylglycerols, cardiolipin; sphingolipids, e.g., spingomyelin; glycolipids, e.g., cerebrosides, gangliosides; in particular also synthetic glycolipids such as 6-(1-thiodesoxy-$\beta$-D-galactopyranosyl)-1-(5-cholesten-3$\beta$-yloxy)-hexane.

Also suitable are the following groups of substances which mostly form double-layers with other amphiphilic bilayer-forming substances in aqueous phase: fatty acids of, preferably, 8 to 24 carbon atoms as well as their esters, salts and amides; alkyl ethers of, preferably, 8 to 24 carbon atoms; alkyl ether derivatives of, preferably, 8 to 24 carbon atoms, such as 1,3-propanediolphospholipids; higher alkylamines of, preferably, 8 to 24 carbon atoms, e.g., stearyl amine; fatty alcohols of, preferably 8 to 24 carbon atoms (e.g., stearyl alcohol), as well as their esters (e.g., dicetyl phosphate); higher alkylthiols of, preferably, 8 to 24 carbon atoms, etc. Furthermore, mixtures of these substances are also suitable. In general, the alkyl chains of the cited substances can be straight, branched and/or cyclic.

Polymerizable derivatives of substances of all the above-mentioned groups of substances, such as, for example, diacetylene-phospholipids, can also be used as bilayer-forming agents, it being possible for these derivatives to be cross-linked in the double layer by known methods, after formation of the liposome.

Mixtures of bilayer-forming substances can be used for all techniques, e.g., often 2–5 different substances are used.

Substances from the following groups can advantageously be used as solubilizing agents:

1. Cholic acid and salts and derivatives thereof, such as deoxycholic acid, taurocholic acid, chenodeoxycholic acid, lithocholic acid and glycocholic acid, the sodium salts preferably being employed.

2. Monomeric or oligomeric sugar derivatives, known as glycosides, with a lipophilic side chain, such as 1-0-n-octyl-$\beta$-D-gluco-pyranoside and the corresponding hexyl, heptyl and nonyl analogues, mixtures of such glycosides also being particularly suitable.

3. Ionogenic substances, of which possible anionic solubilizing agents are the sodium and potassium salts of fatty acids of, preferably, 8 to 24 carbon atoms, amine soaps (e.g., triethanolamine stearate), salts of sulfuric and sulfonic acid esters of higher fatty alcohols of, preferably, 8 to 24 carbon atoms (e.g., sodium lauryl-sulfate, docusate sodium salt U.S.P. 20 or sodium laurylsulfonate), and possible cationic solubilizing agents are, for example, quaternary ammonium compounds.

4. Other non-ionic solubilizing agents such as, for example, fatty acid partial esters of polyhydric alcohols (glycerol monostearate und pentaerythritol monostearate), fatty acid partial esters of sorbitan (Span ® and Crill ®), fatty acid partial esters of polyoxyethylene sorbitan (Tween ®), reaction products of castor oil or hydrogenated castor oil with ethylene oxide (e.g., Cremophor ® EL), ethoxylated saturated fatty alcohols (e.g., Cremophor ® A and O, Brij ®), polyethyleneglycol esters of fatty acids (e.g., Cremophor ® AP, Myrj ®), polyetheralcohols (e.g., Pluronic ®) and polyethylene glycols (Triton ®).

Mixtures of solubilizing agents can be used for all techniques, e.g., often 2–3 different agents are used.

The detergent and bilayer-forming substances form a ternary system with water, which is referred to here as a mixed micelle. The colloidal solution of the mixed micelle, which is subsequently called the micelle solution, can additionally contain electrolytes (predominantly physiologically compatible inorganic salts such as sodium chloride, sodium mono- and di-hydrogenphosphate, potassium mono- and di-hydrogenphosphate, etc.), sorption promoters (such as organic solvents, fatty alcohols and fatty acid esters, etc.), auxiliaries (such as stabilizers and preservatives), peptides, proteins, nucleic acids, lipids, antigens and antibodies, and also active substances with biological and pharmacodynamic properties, etc. Suitable active substances include, for instance, medicinally active compounds and their derivatives such as sterols, e.g., cholesterol, sitosterol, etc.; estrogens, e.g., estrone, estradiol and its esters, ethinylestradiol, etc.; gestagens, e.g., norethisterone acetate, chlormadinone acetate, etc.; corticoids, e.g., hydrocortisone, cortisone, prednisolone, prednisone, dexamethasone, betamethasone, fluprednylidene, etc. and their esters, e.g., hydrocortisone-21-acetate, -21-palmitate, -21-stearate, cortisone-21-acetate, -21-palmitate, -21-stearate, prednisolone-21-acetate, -21-palmitate, -21-stearate, prednisone-21-acetate, -21-palmitate, -21-stearate, dexamethasone-21-acetate, -21-palmitate, -21-stearate, -21-phosphate, betamethasone-21-acetate, -21-palmitate, -21-stearate, -21-phosphate, beta-methasone-17-valerate, fluprednylidene-21-acetate, etc.; peptide hormones such as calcitonin; antibiotics, e.g., tetracyclins, penicillins, cephalosporins, aminoglycosides such as gentamicin, tobramycin, amikacin, kanamycin, neomycin, framycetin, streptomycin or netilmicin; chloroamphenicol; macrolide antibiotics such as erythromycin and its derivatives, particularly its palmitate and stearate, or spiramycin, etc.; antimycotics and dermatics, such as clotrimazol, miconazol, dithranol, benzoyl peroxide, etc.; antiphlogistics such as indometacin, methyl, benzyl or 2-butoxyethyl nicotinate, etc.; zytostatics such as daunorubicin. Furthermore, cosmetically active agents are suitable, e.g., light protecting agents or agents, for the care of the skin.

The amount of these additional compounds can vary within wide limits and are chosen to achieve intended effects where necessary using routine preliminary experiments. For example, amounts of electrolytes or buffers are chosen to be effective to achieve desired ionic strengths or pH's, respectively. Amounts of active ingredients are chosen to achieve desired dosages, i.e., percentage contents per unit weight of liposome. Generally, the amount of such an additional component will suitably vary in the range of 0.1–50 mg/ml in the micelle solution.

Depending on the mode of administration, liposomal medicaments can be converted into the suitable forms of administration:

parenteralia, in particular sterile injection and infusion solutions, it being possible to subject a colloidal solution of the liposomal medicament to antimicrobial treatment. For long-term stability, it may be advantageous to store the liposomal medicament as a lyophilisate with a defined residual content of aqueous phase, and to add the required amount of aqueous phase immediately before administration.

solutions, in particular syrups and eye and nose drops, which, in addition to the liposomal medicaments to be prepared as described above, can contain the additives specific for this medicament form.

non-dosable aerosols and dosable aerosols which, in addition to the liposomal medicaments described above, can contain propellants and stabilizers.

emulsions, in which the liposomal medicaments are always in the aqueous phase and which can be used for parenteral, oral or topical administration. Such emulsions can likewise be processed into the corresponding non-dosable aerosols and to dosable aerosols.

hydrogels which contain the liposomal medicaments are also suitable as possible forms of administration.

lyophilizates, as well as finely dispersed mixtures of amphiphilic bilayer-forming substances, solubilizing agents, pharmaceutical substances and/or pharmaceutical auxiliaries which have been prepared by another route, can also be brought into the required form of administration (tablets, dragees or capsules) and, after administration, can be directly converted into liposomal medicaments by contact with the body fluids.

Unless indicated otherwise herein, all details of the formation and use of the liposomes of this invention are fully conventional and disclosed, e.g., in D. Papahadjopoulos, "Liposomes and their uses in biology and medicine" Ann. N.Y. Acad. Sci. USA 308, 1–462 (1978); R. L. Juliano & D. Layton, "Liposomes as a drug delivery system" in Drug delivery systems p. 189–236, Oxford University Press, Inc., New York, 1980, whose disclosure is incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Example 1 (dilution)

65 mg of egg lecithin in ethanolic solution was evaporated to dryness in vacuo and were resuspended in 5 ml of a 1 mM phosphate buffer of pH 7.3, which had been adjusted to an ionic strength of 0.16 with NaCl. 51.1 mg of solid sodium cholate was added to this dispersion and the mixture stirred at room temperature, whereupon the required associates were formed. This was indicated by the aqueous phase becoming clear. The amount of bilayer-forming substance and solubilizing agent employed for this experiment resulted in a molar ratio of bilayer-forming agent to solubilizing agent of 0.72.

The aqueous phase containing the associates was now diluted with phosphate buffer (1 mM, pH 7.3, ionic strength 0.16) in a ratio of 1:10 at room temperature, whereupon liposomes were formed, which could be seen from the fact that the solution became opalescent.

If necessary, the residual content of sodium cholate can be separated off by means of dialysis of the aqueous phase containing the liposomes or by gel chromatography.

Liposomes prepared under these conditions were unilamellar, with a diameter of 30 nm±2 nm and were extremely homogeneous in respect of their size distribution.

With an initial ratio of bilayer-forming agent to solubilizing agent of 1.15, the solution containing the associates diluted in the ratio of 1:3, homogeneous unilamellar liposomes likewise result, with a diameter of 44±2 nm.

Further preparations of homogeneous unilamellar liposomes of varying size obtained with various bilayer-forming substances and solubilizing agents by dilution as described above, in some cases with incorporation of lipophilic and hydrophilic model pharmaceutical substances, are listed in the table which follows.

TABLE

| BILAYER-FORMING SUBSTANCE Concentration in the aqueous phase during associate formation (mg/ml) | SOLUBILIZING AGENT Starting concentration (mg/ml) | MOLAR RATIO Bilayer-forming agent/ solubilizing agent | MODEL SUBSTANCE Amount employed, based on the aqueous phase (mg/ml) |
|---|---|---|---|
| EYL/ 3:1(*) 9.75 | DSPC Na cholate 3.34 9.11 | 0.8 | — |
| EYL/ 3:1(*) 9.75 | DSPC $C_8$-glycoside 3.34 24.75 | 0.2 | — |
| DSPC 15.81 | Na cholate 43.05 | 0.2 | — |
| EYL 8.0 | $C_7$-glycoside 26,67 | 0.13 | cholesterol 0.81 |
| EYL/cholesterol[1] 5:1(*) 10.4 | $C_8$-glycoside 1.73 50.0 | 0.25 | 6-carboxy-fluorescein 37.63 |

| DILUTION RATIO | LIPOSOME SIZE Diameter (nm) | INCORPORATION RATE Model substance in % of the starting amount | EXPERIMENTAL CONDITIONS |
|---|---|---|---|
| 1:5 | 60.5 | — | Associate solution prepared at 56° C. Dilution at room temperature or 56° C. |
| 1:5 | 126 | — | Associate solution prepared at 56° C. Dilution at room temperature or 56° C. |
| 1:5 | 91.4 | — | Associate solution prepared at 60° C. Dilution at 60° C. |
| 1:3 | 99 | 80 | Associate solution prepared at room temperature. Dilution at room temperature[2] |
| 1:4 | 190 | 3 | Associate solution prepared at 55° C. Dilution at 55° C.[3] |

[1]In this case, cholesterol is to be regarded as a component of the membrane
[2]Non-bonded model substance separated off by means of gel chromatography or dialysis
[3]Non-bonded model substance separated off by means of gel chromatography
(*)Molar ratio
Abbreviations
EYL = egg lecithin
DSPC = distearoyl phosphatidylcholine
$C_8$-glycoside = 1-0-n-octyl β-D-glucopyranoside
$C_7$-glycoside = 1-0-n-heptyl β-D-glucopyranoside Experiments were also carried out to determine the effect of the rate of dilution of aqueous phases containing associates on the size of the liposomes formed. In these, in each case a predetermined amount of additional aqueous phase was added to the aqueous phase containing the associates, while stirring this phase, within various periods of time.

In a first experiment, associates of egg lecithin and sodium cholate in a molar ratio of 0.72 were prepared. The concentration of the egg lecithin was 26 mg/ml. Dilution was effected in a ratio of 1:11 at pH 7.1 and at room temperature. The results were as follows:

| Duration of the dilution process | Diameter of the resulting liposomes in nm | Homogeneity |
| --- | --- | --- |
| about 10 mseconds | 30 | very good |
| 30 minutes | 47 | good |
| 100 minutes | 66 | good |
| >3 hours | could not be determined | heterogeneous |

In a second experiment, associates of egg lecithin and octyl glucoside in a molar ratio of 0.2 were prepared. The concentration of the egg lecithin was 20 mg/ml. Dilution was effected in a ratio of 1:5 at pH 7.1 and at room temperature. The following results were obtained:

| Duration of the dilution process | Diameter of the resulting liposomes in nm | Homogeneity |
| --- | --- | --- |
| about 10 mseconds | 113 | good |
| 24 minutes | 167 | good |
| 50 minutes | 190 | good |
| 3 hrs. 25 minutes | about 240 | heterogeneous |

In a third experiment, associates of distearoyl phosphatidylcholine and sodium cholate in a molar ratio of 0.70 were prepared. The concentration of the distearoyl phosphatidycholine was 50 mg/ml. Dilution was carried out in a ratio of 1:21 at pH 7.1 and 60° C. The results were as follows:

| Duration of the dilution process | Diameter of the resulting liposomes in nm | Homogeneity |
| --- | --- | --- |
| about 10 mseconds | 52 | good |
| 36 minutes | 100 | good |
| 3 hrs. 46 minutes | could not be determined | heterogeneous |

These experiments show that unilamellar liposomes can also be obtained if the dilution process extends over a certain period of, for example, up to about 3 hours, and that the size distribution of the liposomes is homogeneous also in this case, if the dilution rate is kept constant. In any case, however, the dilution rate may not fall below a certain minimum value, because multilamellar liposomes with a heterogeneous size distribution are otherwise formed.

Example 2 (dialysis)

100 mg of egg lecithin in ethanolic solution is evaporated in vacuo and 10 ml of a 1 mM phosphate buffer of pH 7.4, which had been adjusted to an ionic strength of 0.16 with NaCl and contained 190.4 mg of 1-0-n-octyl β-D-glucopyranoside, were added at room temperature, whereupon the required associates were formed immediately.

This associate solution was dialyzed counter-currently at room temperature at a flow rate of 0.2 ml/minute for 60 minutes, separated from dialyzing liquid by means of a semipermeable membrane with a molecular weight exclusion limit of 10,000. The flow rate of the dialyzing liquid (1 mM phosphate buffer of pH 7.4, ionic strength 0.16) was 2.2 ml/minute. The unilamellar liposomes formed from the associates in aqueous solution after this contact time had a diameter of 120 nm and were extremely homogeneous in respect of their size distribution, the residual content of solubilizing agent being 2.6% of the initial content. Formation of the liposomes was completed after 10 minutes.

Enrichment of liposomal medicaments prepared by means of countercurrent dialysis with additional pharmaceutical substances and/or pharmaceutical auxiliaries can be carried out by adding the desired amount of these substances to the dialysing liquid during or after preparation of the liposomal medicament. A defined enrichment of the substances added in the aqueous phase containing the liposomes and, if a suitable temperature is chosen, an increased absorption of these substances into the liposomes is thereby made possible.

Example 3 (jump in temperature)

Distearoyl phosphatidylcholine (DSPC) was converted into a lipid film with the addition of sodium cholate in a molar ratio of 0.2 as described, and the associates were formed at 60° C. by adding 10 mM phosphate buffer of pH 7.1. The lipid concentration of the clear associate solution was 5 mg/ml. When this associate solution was allowed to cool slowly to room temperature, homogeneous unilamellar liposomes with a mean diameter of 260 nm were formed within 4 hours. When this jump in temperature was over a greater range, for example from 60° C. to 4° C., and was correspondingly more rapid, smaller homogeneous liposomes with a mean diameter of 75 nm resulted.

Example 4 (jump in pH)

Phosphatidylcholine from egg yolk was converted into a lipid film with the addition of sodium cholate in a molar ratio of 0.72 as described, and the associates was formed at room temperature by adding 10 mM phosphate buffer of pH 7.1. The lipid concentration of the clear associate solution was 26 mg/ml. When the pH of this clear associate solution was reduced to pH 3 by rapidly adding 0.1N hydrochloric acid, the solubilizing agent was precipitated, homogeneous liposomes with a mean diameter of 30 nm being formed in the supernatant liquor.

Example 5 (increasing the bilayer-forming substance concentration)

100 mg of phosphatidylcholine from egg yolk together with 60 mg of sodium cholate, from which a molar ratio of lecithin to sodium cholate of 0.8 resulted, was converted into a lipid film as described, and the associates were formed at room temperature by adding 5 ml of 10 mM phosphate buffer of pH 7.1. 49.75 mg of phosphatidylcholine were lyophilized in a second vessel. The associate solution (5 ml) described above was added instantaneously to this highly disperse lyophilisate, with stirring; liposomes with a mean diameter of 70 nm spontaneously formed as a result of the change in the molar ratio of bilayer-forming substance to solubilizing agent from originally 0.8 to 1.2.

The embodiments described are in most cases based on conditions wherein the amount of solubilizing agent initially employed is sufficient for the entire amount of bilayer-forming substance present to be solubilized (that is, is present in the form of associates), and that the solubilizing agent content is then reduced to the extent such that liposomes are formed from all the associates in the aqueous phase. However, neither of these factors are necessary in all cases. On the one hand, it is also possible to start with an aqueous phase which, in addition to associates, also contains bilayer-forming substance which is still dispersed, or is in contact with such a substance (for example in film form). On the other hand, it is also possible to reduce the solubilizing agent content only relatively little, so that only some of the associates in the aqueous phase combine to form liposomes, while other associates remain as such. It is even possible also to apply the two possibilities together and then to obtain a product which contains dispersed bilayer-forming substance, associates and liposomes.

Example of an application: hydrogel (a) In analogy to Example 1, 320 mg of egg lecithin, 80 mg of cholesterol and 40 mg of betamethasone 17-valerate were dissolved in ethanol. The solution was evaporated to dryness, the residue resuspended in 20 ml of phosphate buffer, and 400 mg of sodium cholate added. Thereafter, the procedure of Example 1 was followed.

(b) In 75 ml of water, there were dissolved 0.2 g of potassium sorbate, 0.224 g of $Na_2HPO_4.12H_2O$ and 0.64 g of $KH_2PO_4$. With light warming and vigorous stirring, 2 g of hydroxyethyl cellulose was dissolved in the solution obtained. After 0.5 hour of standing, 2 g of glycerol was added with stirring, followed by the liposome dispersion obtained according to (a). The volume of the mixture was adjusted to 100 ml by adding water.

The obtained hydrogel contained 0.04% of active substance and had a pH value of 5.8 to 6.3.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing liposomal medicaments from non-liposomal associates of at least one amphiphilic bilayer-forming substance and a solubilizing agent therefor in an aqueous phase, comprising, increasing the molar ratio of the bilayer-forming substance to the solubilizing agent in such associates, at a rate which is essentially constant in time and location and which is sufficiently high for the associates to combine to form liposomes essentially all of which have a predetermined number of double layers, and which have a predetermined essentially homogeneous size, wherein the increase in molar ratio is effected by lowering the concentration of free dissolved solubilizing agent in the aqueous phase by diluting the aqueous phase.

2. A process of claim 1, wherein the total concentration of solubilizing agent in the aqueous phase is reduced to at most 50% of the starting concentration by dilution with additional aqueous phase.

3. A process of claim 1, wherein the total concentration of solubilizing agent in the aqueous phase is reduced to at most 25% of the starting concentration by dilution with additional aqueous phase.

4. A process of claim 1, wherein the resultant liposomes or liposomal medicaments are incubated with at least one pharmaceutical substance or pharmaceutical auxiliary directly at or above the transition temperature of the bilayer forming substance whereby the pharmaceutical substance or pharmaceutical auxiliary is absorbed or incorporated into the liposomes.

* * * * *